Aug. 11, 1936. J. A. KIRK Re. 20,061

COMBINATION OF OS UTERI LOCATING DEVICE AND MEDICAL APPLICATOR

Original Filed June 18, 1934

INVENTOR

John Andrew Kirk

Reissued Aug. 11, 1936 Re. 20,061

UNITED STATES PATENT OFFICE 20,061

COMBINATION OF OS UTERI LOCATING DEVICE AND MEDICAL APPLICATOR

John A. Kirk, Detroit, Mich.

Original No. 1,978,677, dated October 30, 1934, Serial No. 731,092, June 18, 1934. Application for reissue December 4, 1934, Serial No. 755,939

18 Claims. (Cl. 128—239)

This invention relates to improvements in a vaginal applicator, a device for various uses in the medical and surgical arts and more particularly to an instrument in the science of gynecology, for the effective treatment of uterine disorders such as diseased os and other ailments. The invention embodies improvements involving combined mechanical means for locating the cervix uteri without the use of vaginal illumination, and, having effected this, of applying self-contained medication in jelly or powder form directly to the spot requiring medication, without the liability of loss or waste of the medicated material.

In the medical profession it is a well known fact that in many women the os uteri lies distant from the major labia and out of reach of the fingers; that it is imbedded in a mass of lobes, folds and other vaginal tissue; and that its position in the ceiling or the vagina varies greatly even in the same person from time to time, even during the same day, making its exact location difficult or impossible to ascertain in such cases without vaginal illumination or the use of instruments. The effective medication of afflicted parts is therefore difficult or impossible except by flooding the surrounding healthy parts with medication in the hope that some of the medicinal material will reach the desired spot.

Such difficulties are overcome in the present invention, a principal object of the same being to provide a practical, readily accessible combination device for locating the os and a self-contained medication-expelling appliance immediately ready to apply the medication.

Another object of the present invention is to provide a device light in weight, yet sturdily and economically made of hard rubber or other suitable material and also kept in an aseptic condition, free from angles, sharp edges such as might cause injury to delicate membranes, and also free from openings or crevices which are liable in use to furnish lodging places for foreign or undesirable matter; a device capable of vaginal insertion without the need of any secondary appliance or manipulation, and which can be readily inserted and placed by a physician, but which can also be easily inserted and placed by the patient for self-application when no physician is readily available, through which the efficiency of the device for intra-vaginal medication is increased.

Still a further object of my invention is to provide a vaginal applicator having its stem bent to an obtuse angle at a point intermediate the medicinal container and the applicator, whereby upon rotation of the stem around the axis of that portion adjacent to the container, the applicator end will gyrate bodily to thereby assist in positioning the device.

Still a further object of my invention is to provide a soft rubber cup shaped applicator which has a feeler projecting forwardly from one portion of its rim, the feeler assisting in conducting the applicator to position.

Still a further object of my invention is to provide a cup shaped applicator of soft rubber, the stem of the device projecting through the bottom of the cup member, and having a detachable cap secured over the applicator end of said stem to thereby prevent contamination of the medicant in the stem. The portion of the cup member around the stem is materially thicker than the rim of the cup member to thereby give rigidity to the device without detracting from the advantages of the soft rubber applicator.

Other objects of my invention, which is designed with a view to efficiency, economy, and simplicity of construction, will become more apparent from the description hereinafter following, which covers a preferred embodiment of the same, reference being had to the accompanying drawing in which—

Like characters designate corresponding parts throughout the several views.

Figure 1:
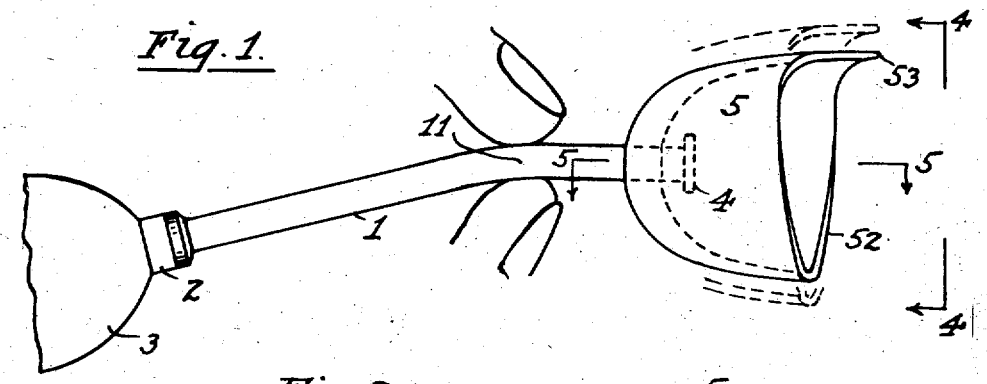
Figure 1 is a side elevation.

1 is the stem of hollow construction, provided at one end with a screwed portion 2 adapted for connection to a compressible bulb 3 of conventional form adapted to contain the medicant which it is desired to employ, while the other end is provided with a screw cap 4 or other suitable closure. Surrounding the stem 1 and in spaced relation to the screw cap 4 is the cup-shaped applicator member 5 which is in general of hollow, spheroidal shape having a relatively thick edge 51 at its point of connection with the stem, the said edge being of relatively hard rubber or other suitable material and terminating in a thin edge 52 of rubber or other comparatively soft material. A cross section through the rim of the cup is of oval shape so that rotation of the cup tends to spread the lobes and vaginal tissue.

The edge 52, instead of being circular, is made in the form of a helix terminating in a peak 53 which is slightly rounded in shape and connected by an inclined edge 54 with the lower portion 55 of the helix.

Figure 2:
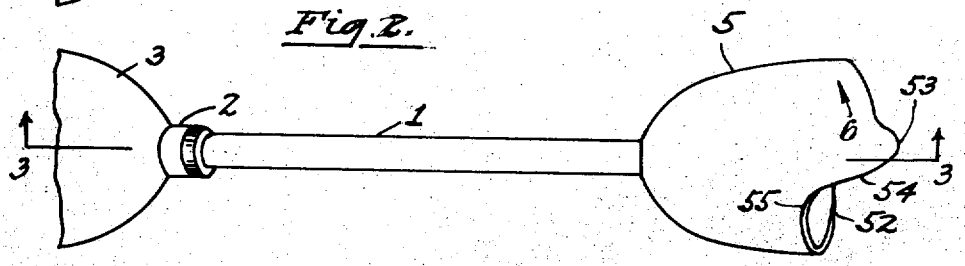
Figure 2 is a plan view.
Figure 3:
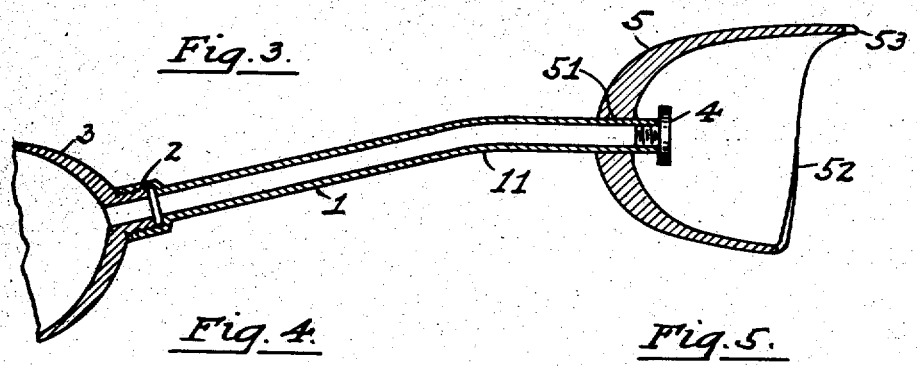
Figure 3 is a section on line 3—3 of Figure 2.
Figure 4:
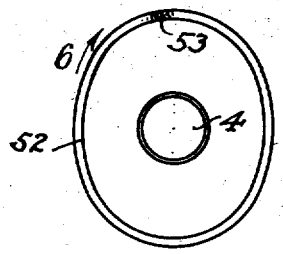
Figure 4 is an end view taken on line 4—4 of Figure 1.
Figure 5:
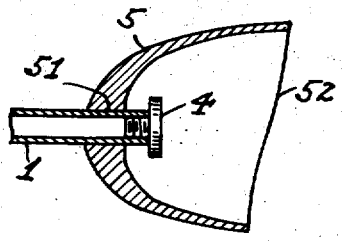
Figure 5 is a fragmentary section on line 5—5 of Figure 1.

The stem 1 is bent at 11 to an angle of approximately ten degrees, as a result of which the device, being inserted into the vagina and rotated in the direction of the arrow 6 in Figures 2 and 4, will move in a gyratory path, as indicated in broken lines in Figure 1, so that, with slight pressure, it will automatically locate itself around the os uterus and thereby ensure the proper application of the medicament at the required point.

The edge 52, terminating in the peak 53, is on an inclined line in order to more effectively push aside the lobes, folds, and other vaginal tissue as the device is rotated and gyrated in the vagina, so that the peak 53, turned slightly outward, will serve as an antenna, or feeler, to direct the applicator past various obstructions. A bent handle or tube is provided so that by holding it with two fingers of one hand (Fig. 1) at the place where the bend occurs (that point serving as an axis) and turning the device with the fingers of the other hand, a gyrating effect is accomplished by making use of the container 3 as a handle. The gyration also serves to push the vaginal tissue aside and aids in locating the os uteri. The user can feel when the device slips over the os uteri. A slight pressure then sets the device in place for the application of the medicament.

It will be understood that, before insertion, the screw cap or closure 4 is removed, so that all that is necessary after insertion is to press upon the bulb 3 so as to discharge the medicated material to the amount required. Thus, great economy of material is effected since it is applied directly to the required part, and after withdrawal of the applicator the screw cap is replaced so as to retain the residual material and prevent the access of dirt or foreign matter thereto.

It will be observed from the foregoing that I have provided a device which is eminently suitable for the purpose intended, and which is entirely self-contained, and while I have herein described a preferred form of the device, it will be understood that various changes may be made without departing from the spirit of my invention, and it is my intention to cover by my claims such changes as may reasonably be included within the scope thereof.

I claim as my invention:

1. A device of the character described comprising a hollow cup-shaped member having a substantially helical edge terminating in a peak adapted to be moved in advance of the body of the helix and to guide the member into position.

2. A device of the character described comprising a hollow stem having at one end a container for material to be applied and proximate to the other end a hollow cup-shaped member having a substantially helical edge terminating in a peak adapted to be moved in advance of the body of the helix and to guide the member into position.

3. A device of the character described comprising a hollow stem having at one end a container for material to be applied and proximate to the other end a hollow cup-shaped member having a substantially helical edge terminating in a peak adapted to be moved in advance of the body of the helix and to guide the member into position, the said member at its junction with said stem being of relatively hard material while its edge is of soft material.

4. A device of the character described comprising a hollow stem having at one end a container for material to be applied and proximate to the other end a hollow cup-shaped member having a substantially helical edge terminating in a peak adapted to be moved in advance of the body of the helix and to guide the member into position, the said member at its junction with said stem being thick and of relatively hard material while its edge is of soft material and of reduced thickness.

5. A device of the character described comprising a hollow stem having at one end a container for material to be applied and proximate to the other end a hollow cup-shaped member having a substantiallly helical edge terminating in a peak adapted to be moved in advance of the body of the helix and to guide the member into position, the said stem intermediate its ends being bent to an obtuse angle and being provided with closure means at its discharge end.

6. A device of the character described comprising a hollow stem having at one end a container for material to be applied and proximate to the other end a hollow cup-shaped member having a substantially helical edge terminating in a peak adapted to be moved in advance of the body of the helix and to guide the member into position, the end of the said stem projecting within the cup member and being provided with closure means.

7. In combination, a hollow stem, and a cup-shaped applicator member having one end of said stem projecting through the bottom thereof so as to form a passage-way through said stem and into said applicator member, said applicator member having a peak projecting a substantial distance from one portion of its rim so as to guide the member into position the remaining portion of said rim being substantially flat.

8. The combination, as claimed in claim 7 wherein said peak is formed of relatively soft rubber which will distort laterally and thus allow the remainder of said rim to form an effective seat.

9. In combination, a hollow stem, an outwardly opening cup shaped applicator having one end of said stem projecting therethrough so as to form a continuous passageway from the stem into the applicator, said applicator being formed of relatively soft rubber with the bottom thereof being at least twice as thick as the rim portion and with a soft rubber peak projecting axially from one portion of the rim, said cup tapering in section from the bottom to its outer edge, for the purpose described.

10. The combination, as claimed in claim 9, wherein a relatively soft rubber peak projects a substantial distance from one portion of the rim, the remaining portion of the rim being substantially flat.

11. In combination, a hollow stem having at one end a container for medicament to be applied and having an applicator at the other end thereof, whereby the medicament may be forced into said applicator through said stem, said stem comprising a straight section which extends from the container a substantial portion of the distance to said applicator with the remaining portion of said stem being bent at an angle thereto, said applicator comprising a cup shaped member having a peak projecting a substantial distance from one portion of its rim, said applicator being fixed to the bent end of said stem in such position that said peak will be in substantial alignment with a continuation of the axis of the container portion of said stem.

12. A device, as claimed in claim 11, wherein the straight section of said stem adjacent to said container extends substantially two thirds of the length thereof.

13. The combination, as claimed in claim 11, wherein said peak is formed of relatively soft rubber, which will distort laterally and allow the remainder of said rim to form an effective seat.

14. The combination, as claimed in claim 11, wherein said applicator is provided with a substantially helical edge which terminates in said peak.

15. In a device of the character described, a hollow stem having at one end a container for material to be applied and having at the other end a cup shaped applying member, said stem comprising a straight section which extends from said container slightly more than half the distance to said applying member, the remainder of said stem extending at such angle to said first portion that a continuation of the axis of said first mentioned portion extends substantially through the rim of said cup shaped member, whereby rotation of the stem upon the axis of its major portion will cause the applicator to gyrate bodily.

16. A device, as claimed in claim 15, wherein the straight portion of said stem extends substantially two thirds of the length thereof so that the device may be readily rotated around the axis of said major portion.

17. A device, as claimed in claim 15, wherein a peak extends outwardly from the rim of said cup shaped applying member, the remaining portion of said rim being substantially flat.

18. A device, as claimed in claim 15, wherein a peak extends outwardly from the rim of said cup shaped applying member, said peak being aligned with the continuation of the axis of the major portion of said stem so as to act as a feeler for said cup member.

JOHN A. KIRK.